United States Patent
Shirai et al.

(10) Patent No.: US 8,641,616 B2
(45) Date of Patent: Feb. 4, 2014

(54) METHOD AND APPARATUS FOR PROCESSING BIO-INFORMATION

(75) Inventors: Katsuya Shirai, Kanagawa (JP); Yoichiro Sako, Tokyo (JP); Toshiro Terauchi, Tokyo (JP); Makoto Inoue, Tokyo (JP); Masamichi Asukai, Kanagawa (JP); Kenichi Makino, Kanagawa (JP); Motoyuki Takai, Tokyo (JP); Yasushi Miyajima, Kanagawa (JP)

(73) Assignee: Sony Corporation, Tokyo (JP)

( * ) Notice: Subject to any disclaimer, the term of this patent is extended or adjusted under 35 U.S.C. 154(b) by 715 days.

(21) Appl. No.: 11/254,022

(22) Filed: Oct. 19, 2005

(65) Prior Publication Data

US 2006/0094934 A1 May 4, 2006

(30) Foreign Application Priority Data

Oct. 19, 2004 (JP) .................. P2004-303659

(51) Int. Cl.
*A61B 5/00* (2006.01)

(52) U.S. Cl.
USPC ........................... 600/301; 600/300

(58) Field of Classification Search
USPC ................... 600/300, 301
See application file for complete search history.

(56) References Cited

U.S. PATENT DOCUMENTS

| | | | | |
|---|---|---|---|---|
| 4,289,121 A * | 9/1981 | Kupriyanovich | ............... | 600/27 |
| 4,315,502 A * | 2/1982 | Gorges | ............... | 600/27 |
| 4,553,534 A * | 11/1985 | Stiegler | ............... | 601/15 |
| 5,047,006 A * | 9/1991 | Brandston et al. | ............... | 600/21 |
| 5,304,112 A * | 4/1994 | Mrklas et al. | ............... | 600/27 |
| 5,518,497 A * | 5/1996 | Widjaja et al. | ............... | 600/27 |
| 5,689,241 A * | 11/1997 | Clarke et al. | ............... | 340/575 |
| 5,920,351 A * | 7/1999 | Takeshima et al. | ............ | 348/379 |
| 6,702,767 B1 * | 3/2004 | Douglas et al. | ............... | 601/15 |
| 7,027,621 B1 * | 4/2006 | Prokoski | ............... | 382/118 |
| 7,091,471 B2 * | 8/2006 | Wenstrand et al. | ............ | 250/221 |
| 7,120,880 B1 * | 10/2006 | Dryer et al. | ............... | 715/863 |
| 7,542,068 B2 * | 6/2009 | Eshkoli et al. | ............. | 348/14.08 |
| 7,742,037 B2 * | 6/2010 | Sako et al. | ............... | 345/156 |
| 8,322,856 B2 * | 12/2012 | Vertegaal et al. | ............. | 351/209 |
| 2002/0010929 A1 * | 1/2002 | Collier | ............... | 725/40 |
| 2003/0052789 A1 * | 3/2003 | Colmenarez et al. | ......... | 340/575 |
| 2004/0107105 A1 * | 6/2004 | Shomi et al. | ............... | 704/270 |
| 2004/0122486 A1 * | 6/2004 | Stahmann et al. | ............. | 607/60 |
| 2004/0193068 A1 * | 9/2004 | Burton et al. | ............... | 600/544 |
| 2004/0210159 A1 * | 10/2004 | Kibar | ............... | 600/558 |
| 2005/0199783 A1 * | 9/2005 | Wenstrand et al. | ........ | 250/214.1 |
| 2006/0232430 A1 * | 10/2006 | Takaoka et al. | ............... | 340/575 |
| 2010/0076333 A9 * | 3/2010 | Burton et al. | ............... | 600/544 |

FOREIGN PATENT DOCUMENTS

| | | |
|---|---|---|
| JP | 61-175129 | 8/1986 |
| JP | 08-257017 | 10/1996 |
| JP | 2000-194854 A | 7/2000 |
| JP | 2002-034936 A | 2/2002 |
| JP | 2003-038494 A | 2/2003 |

* cited by examiner

*Primary Examiner* — Bill Thomson
*Assistant Examiner* — Bobby Soriano
(74) *Attorney, Agent, or Firm* — Wolf, Greenfield & Sacks, P.C.

(57) ABSTRACT

A bio-information processing apparatus includes a bio-information sensor for measuring the bio-information of a subject in a non-contact manner and in an unrestricted manner; and a circuit for estimating the psychological state of the subject and the intensity thereof on the basis of the measured value of the bio-information measured using the bio-information sensor and on the basis of an initial value or a standard value of the measured value.

19 Claims, 7 Drawing Sheets

FIG. 2A

BLINKING

RESPIRATION

FIG. 7A
ORIGINAL IMAGE

C

FIG. 7B
CONVERSION INTO GRAYSCALE

FIG. 7C
DIFFERENCE FROM PREVIOUS FRAME

METHOD AND APPARATUS FOR PROCESSING BIO-INFORMATION

CROSS REFERENCES TO RELATED APPLICATIONS

The present invention contains subject matter related to Japanese Patent Application JP 2004-303659 filed in the Japanese Patent Office on Oct. 19, 2004, the entire contents of which are incorporated herein by reference.

BACKGROUND OF THE INVENTION

1. Field of the Invention

The present invention relates to a method and apparatus for processing bio-information (biometric information).

2. Description of the Related Art

It has been considered that the bio-information of a subject is detected using a sensor and the emotion and the psychological state of the subject are estimated from the detected bio-information.

For example, there is a known method in which electrocardiographic detection means and a pulse sensor are attached to the body of a subject in order to measure the heartbeat rate and the pulse rate, and the tension level of the subject or changes in the emotion of the subject are estimated from the variations thereof (refer to, for example, Japanese Unexamined Patent Application Publication Nos. 1995-323162 and 2002-23918).

There is also a known method in which the tension level and changes in the emotion of the subject are estimated by measuring the heartbeat rate and the pulse rate using a sensor attached directly on the finger tip or the wrist of the subject by using a sensor attached to a necklace, glasses, a card, or a pedometer of the subject. Alternatively, there is also a known method in which the degree of conformity between the pulse rates of another party and the subject during personal negotiations is evaluated and the degree of conformity with the other party (the degree of withdrawal in a withdrawal phenomenon) is estimated (refer to, for example, Japanese Unexamined Patent Application Publication Nos. 2002-23918 and 1999-4892).

Furthermore, there is also a known method in which infrared rays are irradiated onto the eyes of the subject, and the blinking of the subject is detected on the basis of the changes in the amount of light of the reflected light in order to estimate the psychological state, such as dozing off and being interested, is estimated (refer to, for example, Japanese Unexamined Patent Application Publication No. 2002-35523). There is also a known method in which ultrasonic waves are irradiated onto the subject, and the movement of the body of the subject is captured on the basis of the changes in the level of the reflected waves in order to estimate dozing off (refer to, for example, Japanese Unexamined Patent Application Publication No. 1992-212331).

SUMMARY OF THE INVENTION

However, when the psychological state is estimated using the above-described method, in the case of a contact-type bio-information sensor, not only is the attachment of the sensor troublesome, but also a user becomes conscious about the sensor as a result of the attachment thereof, causing psychological influences to appear in the measurement result. In the case of a non-contact-type bio-information sensor, since infrared rays and ultrasonic waves are irradiated onto the human body, there are cases in which it is difficult to ignore the influence on the human body.

It is desirable to solve the above-described problems.

According to an embodiment of the present invention, there is provided a bio-information processing apparatus including: a bio-information sensor for measuring the bio-information of a subject in a non-contact manner and in an unrestricted manner; and a circuit for estimating the psychological state of the subject and the intensity thereof on the basis of the measured value of the bio-information measured using the bio-information sensor and on the basis of an initial value or a standard value of the bio-information.

According to the embodiment of the present invention, the arousal level of the subject and the concentration level (or the interested level) with respect to an object can be estimated and also, video and/or sound can be reproduced in a state most appropriate for the psychological state of the subject at that time on the basis of the estimation result.

In that case, the bio-information of the subject can be obtained in a non-contact manner and in an unrestricted manner, the subject does not need to have psychological and physical burdens, and no influence appears in the measurement result. Even if measurements are performed for a long time, no influence is exerted on the body of the subject.

DESCRIPTION OF THE PREFERRED EMBODIMENTS

In an embodiment of the present invention, the bio-information of a subject is obtained in a non-contact manner and in an unrestricted manner, the psychological state and the emotion of the subject are estimated on the basis of the obtained bio-information, and changes are provided to the environment of the subject according to the estimation result.

(1) Example of Video/Audio Reproduction Apparatus (No. 1)

Figure 1:
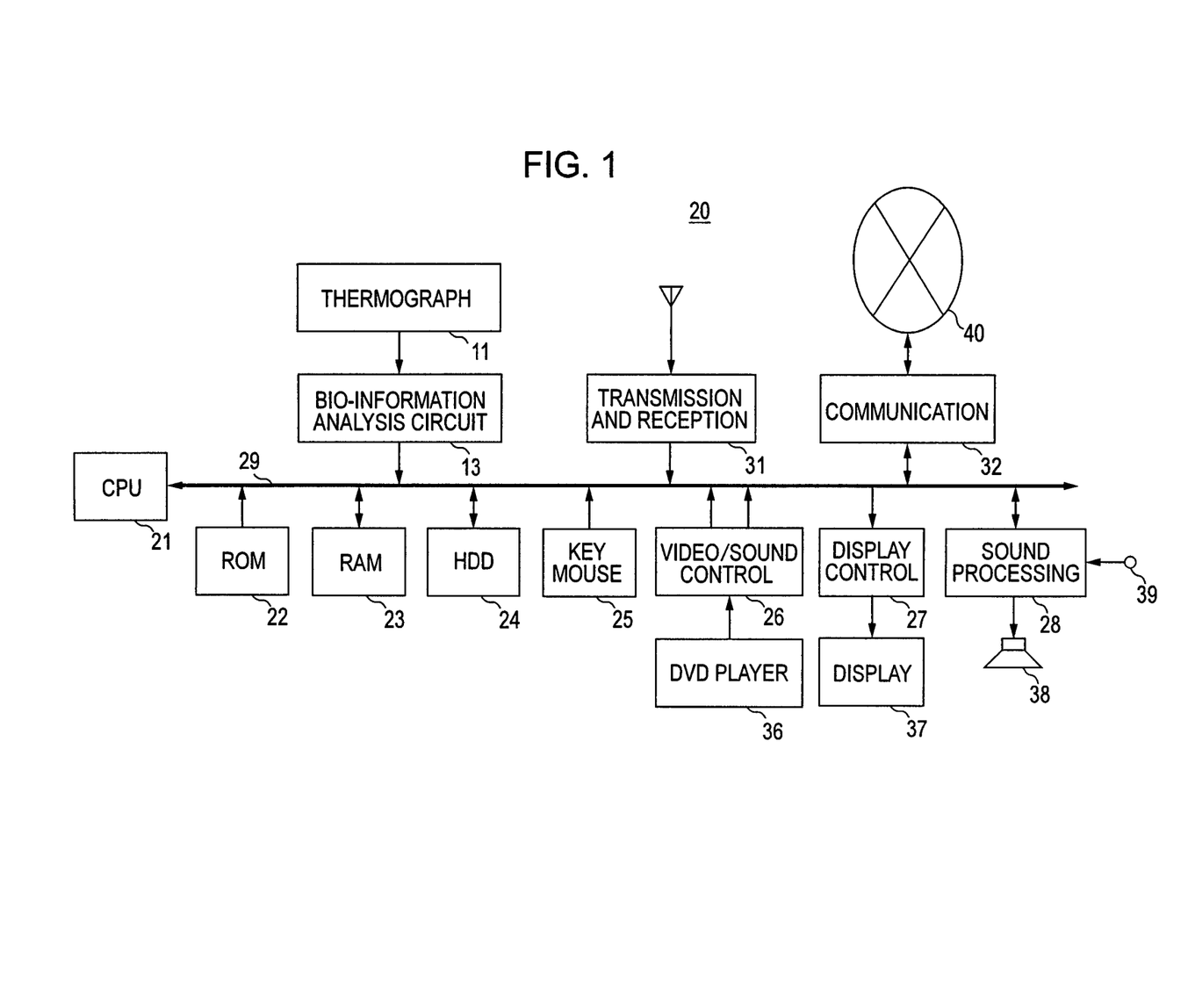
FIG. 1 is a schematic diagram showing an embodiment of the present invention.

FIG. 1 shows an example when the embodiment of the present invention is applied to a video/audio reproduction apparatus. The video/audio reproduction apparatus determines the arousal level and the concentration level with respect to an object as indexes indicating the psychological state of the viewer who is a subject, and controls video and sound reproduced in accordance with the arousal level and the concentration level.

For this purpose, in this example, the video/audio reproduction apparatus has a thermograph (infrared video camera)

Figure 2A:
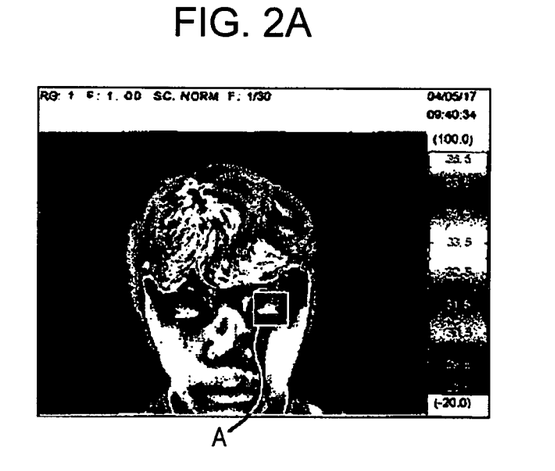
FIGS. 2A and 2B show examples of output data of a bio-information sensor that can be used in the embodiment of the present invention.
Figure 3A:
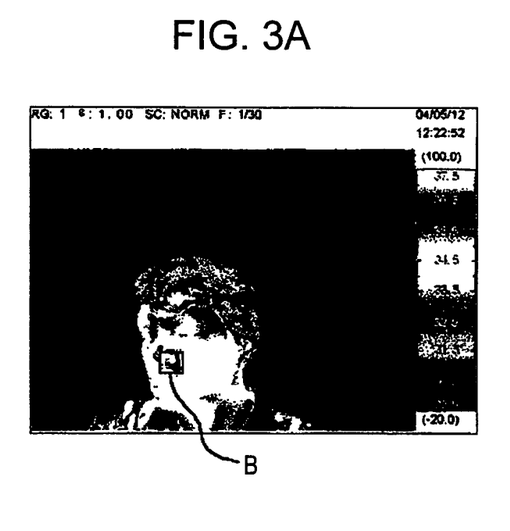
FIGS. 3A and 3B show examples of output data of a bio-information sensor that can be used in the embodiment of the present invention.

11 as a bio-information sensor for obtaining bio-information in a non-contact manner and in an unrestricted manner from the viewer (the subject). Then, as shown in FIG. 2A or FIG. 3A, the surface temperature of the face of the viewer is measured by a thermograph 11, and the measurement output is supplied to a bio-information analysis circuit 13.

In this case, when the viewer opens his/her eye, since the area containing the eye area A (the white frame in FIG. 2A) is the eyeball, the temperature is lower than that of the face. However, when the viewer closes his/her eye, since the eyeball is covered by the eyelid, the area A reaches a temperature that is nearly equal to that of the face.

Figure 2B:
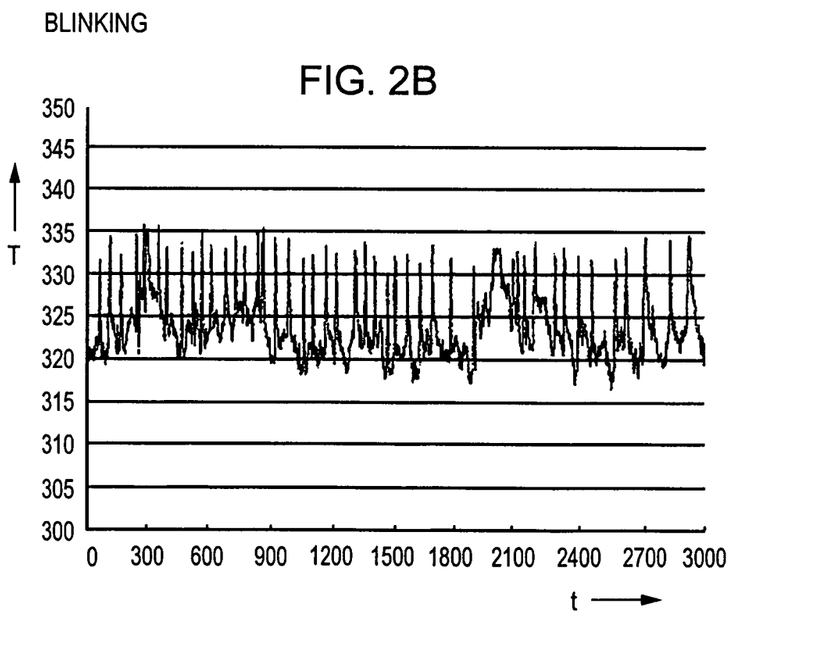

FIG. 2B shows an example of measurement results when the temperature of the area A is measured by a thermograph, in which the horizontal axis t indicates time such that the number of frames of a video signal is the unit and the vertical axis T indicates the temperature of the area A. Among the measurement results, the portion where the temperature is low indicates when the eyelid is opened, and the portion where the temperature is high indicates when the eyelid is closed. Then, in the analysis circuit 13, the value indicating the temperature of the face around the area A is compared with the value indicating the temperature of the area A among the measurement outputs of the thermograph 11, and an analysis result indicating the blinking rate per unit time is extracted.

Furthermore, when the viewer respires, since air warmed inside the body leaves out from the nostrils in the case of expiration, the body surface temperature near the nostrils (the area B indicated by the black frame in FIG. 3A) increases, and in the case of inhalation, since air of a low temperature enters the body, the body surface temperature near the nostrils decreases.

Figure 3B:
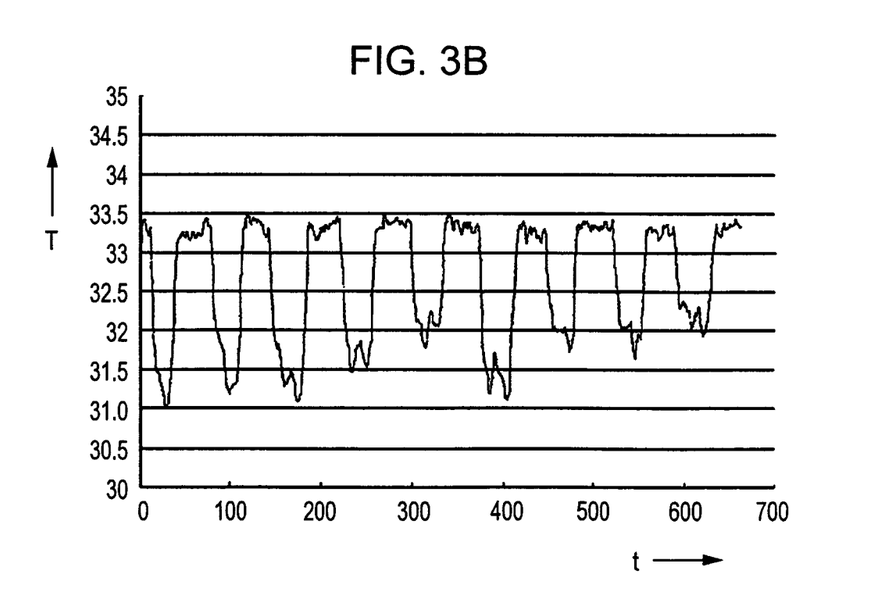

FIG. 3B shows an example of measurement results when the temperature of the area B is measured using a thermograph, in which the horizontal axis t indicates time such that the number of frames of a video signal is the unit and the vertical axis T indicates the body surface temperature of the area B. Among the measurement results, the portion where the temperature is low indicates the period of inhalation, and the portion where the temperature is high indicates the period of expiration. Then, in the analysis circuit 13, the value indicating the temperature of the area B and the value indicating the temperature of the face around the area B among the measurement outputs of the thermograph 11 are compared with each other, and the analysis result indicating the respiration rate is extracted.

Then, the analysis results of the blinking rate and the respiration rate are supplied to a microcomputer 20, whereby the arousal level of the viewer and the concentration level of the viewer with respect to the object are computed on the basis of changes in the blinking rate and the respiration rate, and video and sound are appropriately reproduced in accordance with the results. That is, the microcomputer 20 includes a CPU 21 for executing a program, a ROM 22 in which various kinds of programs are written, and a RAM 23 used as a work area, and these are interconnected to one another via a system bus 29.

Figure 4:
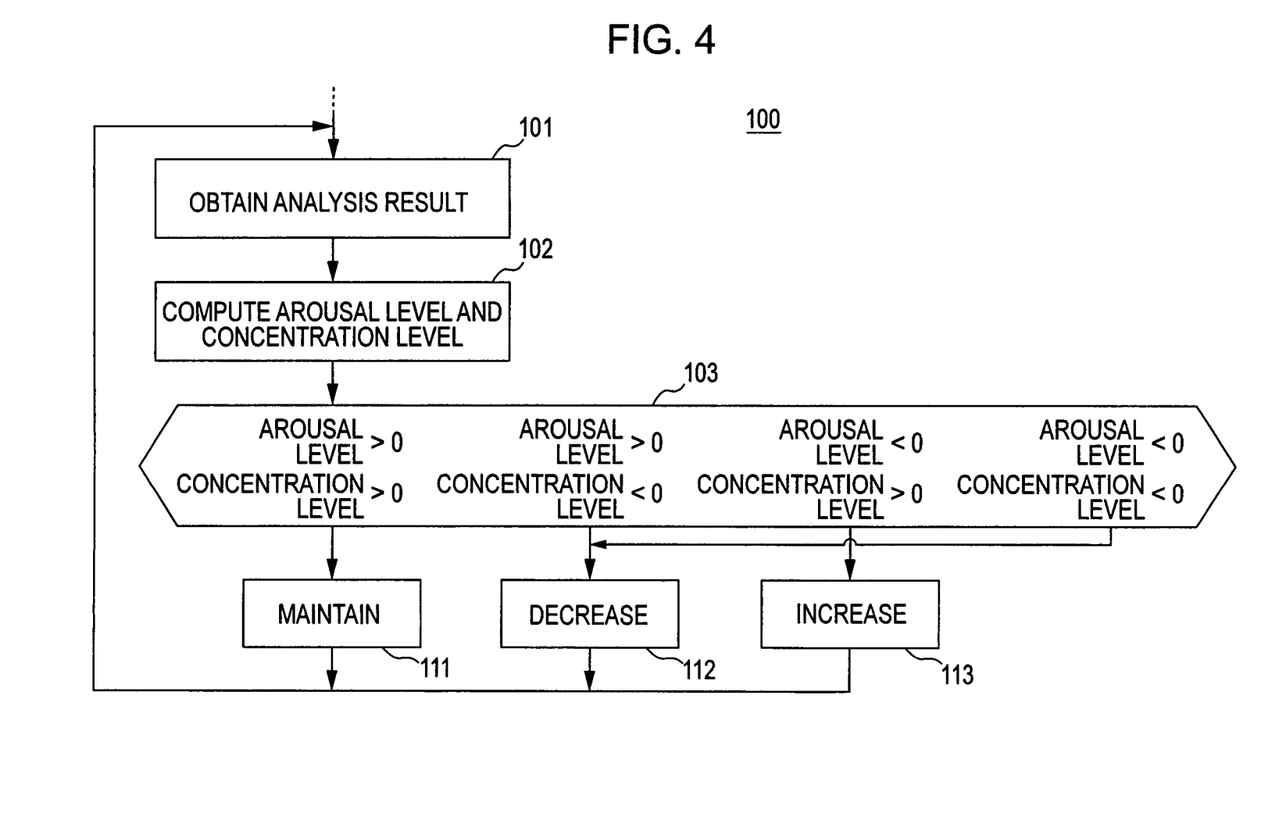
FIG. 4 is a flowchart showing an example of a control flow according to the embodiment of the present invention.

In this case, the ROM 22 is also provided with, for example, a routine 100 shown in FIG. 4 as a part of a program to be executed by the CPU 21. The details of the routine 100 will be described later. The routine 100 is used to control, based on the bio-information of the viewer, a video signal and a sound signal so that the viewer feels comfortable with video and sound. In FIG. 4, for the routine 100, only the parts related to the embodiment of the present invention are extracted and shown.

Furthermore, the microcomputer 20 includes a hard disk device 24 as a large-capacity recording device and a user interface 25 such as a keyboard and a mouse, and these are connected to the system bus 29. In this example, as the signal source for the video signal and the sound signal, a DVD player 36 is provided, and this DVD player 36 is connected to the system bus 29 via a video/sound control circuit 26.

In this case, the video/sound control circuit 26 changes the state of the video image to be displayed, for example, the contrast, the brightness, the hue, and the color saturation level by controlling the video signal reproduced by the DVD player 36 and also, controls the playback speed of the DVD player 36. Furthermore, the video/sound control circuit 26 controls the sound volume, the frequency characteristics, and the reverberation of sound to be reproduced by controlling the sound signal reproduced by the DVD player 36.

A display 37 is connected to the system bus 29 via the display control circuit 27, the video signal output from the video/sound control circuit 26 is converted into a signal for display by the display control circuit 27, and this display signal is supplied to the display 37. Furthermore, a sound processing circuit 28 is connected to the system bus 29, a sound signal is supplied to a speaker 38 via the processing circuit 28, and also, a sound signal from a microphone 39 is received by the microcomputer 20 via the sound processing circuit 28.

In addition, in order to exchange the bio-information of the viewer and data, which are measured by this apparatus and other similar apparatuses, a transmission and reception circuit 31 and a communication circuit 32 are connected to the system bus 29, and the communication circuit 32 is connected to another network, for example, the Internet 40.

In such a configuration, when the user interface 25 is operated, a video signal and a sound signal are reproduced by the DVD player 36. The video signal is supplied via the video/sound control circuit 26 and the display control circuit 27 to the display 37, whereby a video image is displayed, and the sound signal is supplied via the video/sound control circuit 26 and the sound processing circuit 28 to a speaker 38, whereby sound is reproduced.

At this time, the routine 100 is executed by the CPU 21 in order to compute the arousal level and the concentration level of the viewer with respect to the video of the display 37 and the sound of the speaker 38. On the basis of the computation results, the video and the sound are controlled so that the viewer feels comfortable with the video and the sound.

More specifically, when the routine 100 is executed, in step 101, the analysis results (the blinking rate and the respiration rate) from the bio-information analysis circuit 13 are received by the microcomputer 20. Next, in step 102, the arousal level and the concentration level are computed on the basis of the analysis results received in step 101. This computation method will be described later with reference to section (3). The arousal level and the concentration level are computed as analog values that can take positive and negative polarities, respectively.

Figure 5:
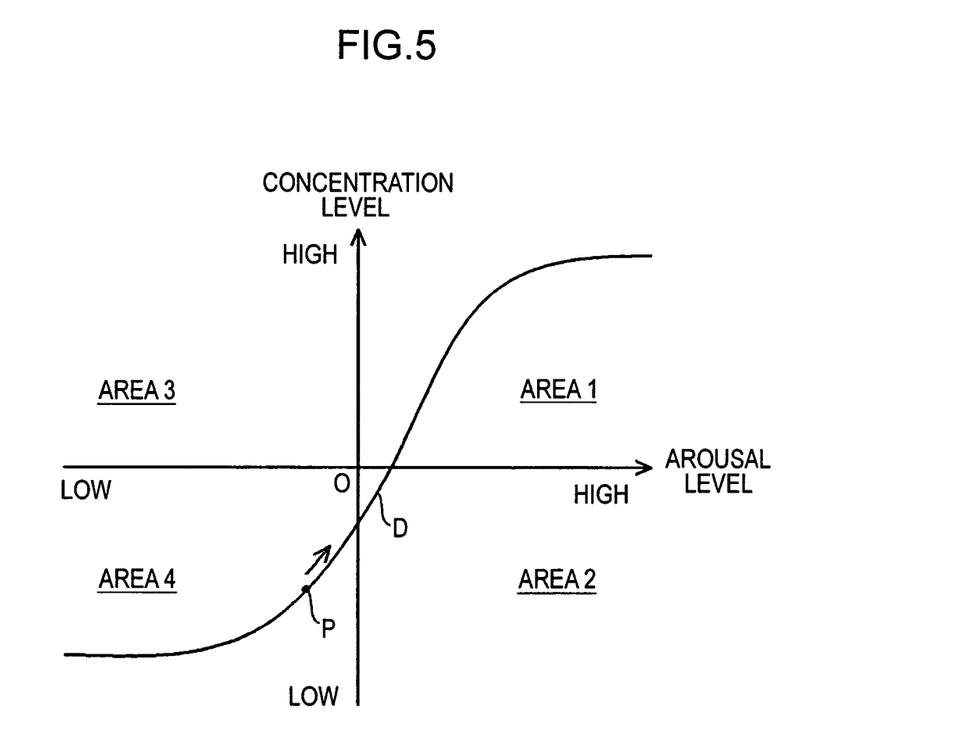
FIG. 5 shows the embodiment of the present invention.

Then, the process proceeds to step 103, where a determination is made as to the polarities of the arousal level and the concentration level computed in step 102, and the process is made to branch depending on the combination of the polarities. That is, the arousal level can take either a positive or a negative value and also, the concentration level can take either a positive or a negative value. Therefore, the arousal level and the concentration level are represented by two-dimensional coordinates, as shown in FIG. 5. At this time, the following is observed:

in the area 1, the arousal level>0 and the concentration level>0 (the arousal level is high and with interest), in the area 2, the arousal level>0 and the concentration level<0 (the arousal level is high but without interest), in the area 3, the arousal level<0 and the concentration level>0 (the arousal level is low but with interest), and in the area 4, the arousal level<0 and the concentration level<0 (the arousal level is low and without interest).

Therefore, when the arousal level and the concentration level fall into the area 1, the psychological state of the viewer at this time is estimated in such a way that the viewer feels comfortable with the video and the sound. The process then proceeds from step 103 to step 111. In step 111, the process returns to step 101 without modifying the video signal and the sound signal that are supplied to the display 37 and the speaker 38. That is, in the case of the area 1, it is determined that the viewer is satisfied with the video and the sound at this time, and the reproduction state is not changed.

However, when the arousal level and the concentration level fall into the area 2, the psychological state of the viewer is estimated in such a way that the viewer is not interested with the video and the sound at this time, and the process proceeds from step 103 to step 112. In step 112, for example, the DC level and the AC level of the video signal supplied to the display 37 are decreased to decrease the luminance and the contrast of the video displayed on the display 37. Furthermore, the level of the sound signal supplied to the speaker 38 is decreased and the frequency characteristics are modified to decrease the volume of the sound output from the speaker 38 in order to decrease the low frequency range and the high frequency range or in order to weaken the rhythm. Thereafter, the process returns to step 101.

When the levels set in step 112 continue for a predetermined period of time, this is the time in which the arousal level and the concentration level of the viewer are not improved. Therefore, at this time, for example, the reproduction of the video and the sound is stopped in step 112.

When the arousal level and the concentration level fall into the area 3, the process proceeds from step 103 to step 113. In step 113, in order to increase the satisfaction level by increasing the arousal level and in order to increase the concentration level, conversely to that in step 112, for example, the DC level and the AC level of the video signal supplied to the display 37 are increased to increase the luminance and the contrast of the video displayed on the display 37. Furthermore, the level of the sound signal supplied to the speaker 38 is increased and the frequency characteristics are modified to increase the volume of the sound output from the speaker 38 in order to increase the low frequency range and the high frequency or in order to strengthen the rhythm. Thereafter, the process returns to step 101.

For example, when the user sets the reproduction apparatus to the sleep mode via the user interface 25, when the levels of the area 3 are reached, the comfortable sleep of the viewer is not disturbed, and therefore, the reproduction state at this time is maintained.

When the arousal level and the concentration level fall into the area 4, the psychological state of the viewer is estimated in such a way that the viewer is dissatisfied with the video and the sound at this time. The process then proceeds from step 103 to step 112, where the dissatisfaction of the viewer is removed similarly to that for the area 2.

Therefore, according to the routine 100, it is possible for the viewer to typically comfortably view the video and the sound.

In this manner, according to the above-described video/audio reproduction apparatus, the arousal level and the concentration level of the viewer (the subject) with respect to the object can be estimated and also, on the basis of the estimation results, the video and the sound can be reproduced in a state most appropriate for the psychological state of the viewer at that time.

Then, in this case, since the bio-information of the viewer can be obtained in a non-contact manner and in an unrestricted manner, the viewer does not feel the annoyance of attaching the sensor and also is not conscious about the sensor. Therefore, the psychological influence does not appear in the measurement results. Furthermore, since the measurement of the bio-information is performed using the thermograph 11, no influence is exerted on the human body even if measurements are performed for a long time.

(2) Example of Video/Audio Reproduction Apparatus (No. 2)

Figure 6:
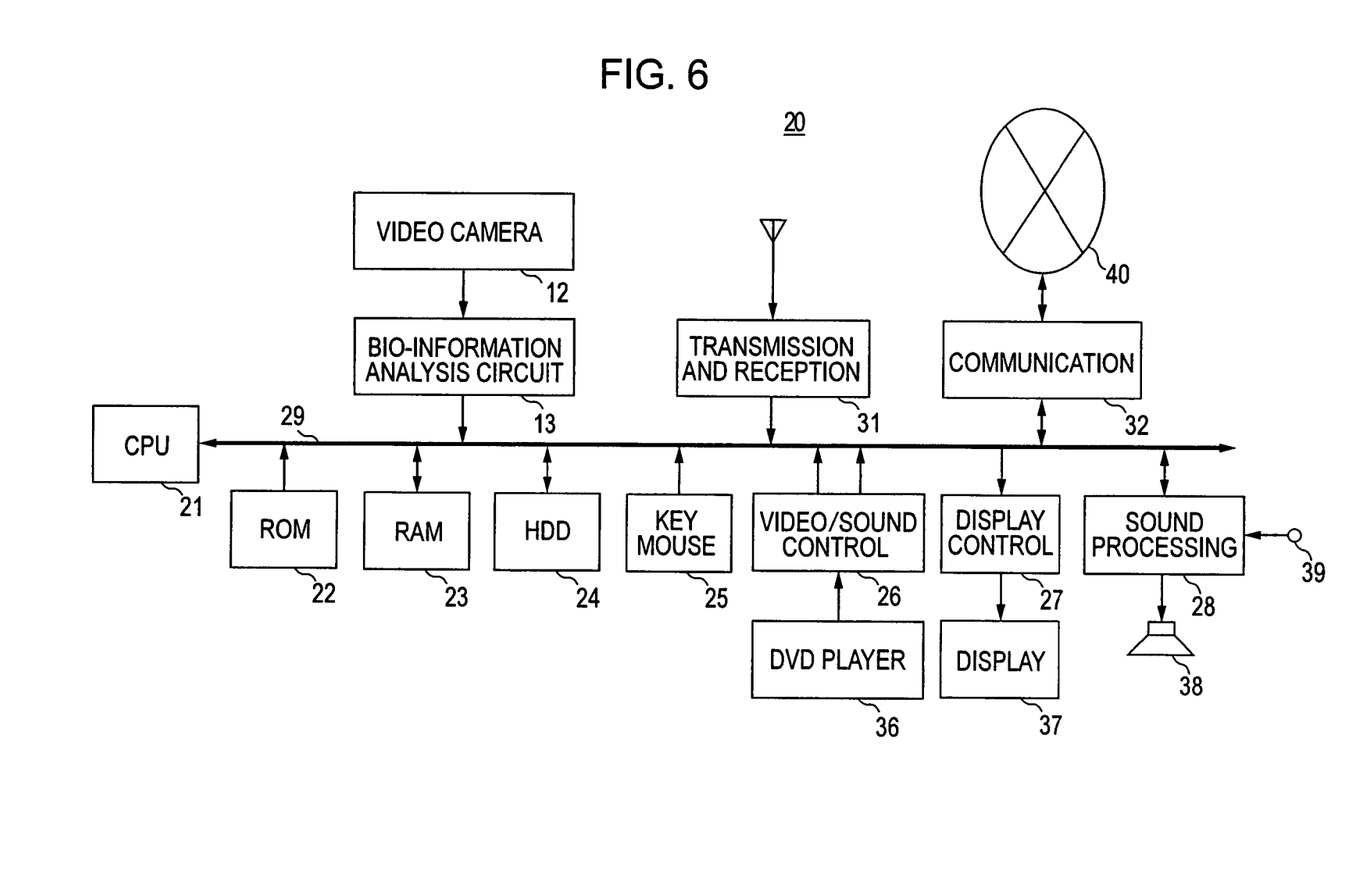
FIG. 6 is a schematic diagram showing another embodiment of the present invention.

FIG. 6 shows a case in which an ordinary video camera 12 is used as a bio-information sensor without contact and restriction in the video/audio reproduction apparatus described with reference to section (1). For example, the full body of the viewer is image-captured by the video camera 12, and the video signal is supplied to the bio-information analysis circuit 13.

Figure 7A:
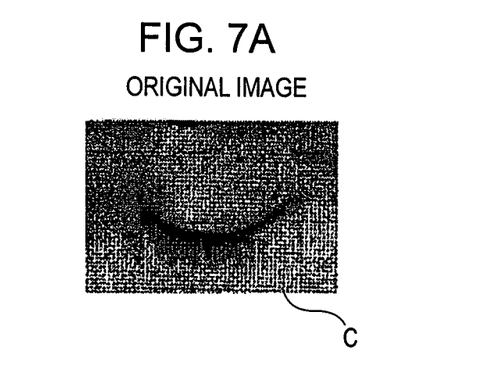
FIGS. 7A, 7B, and 7C show the embodiment of the present invention.
Figure 7B:
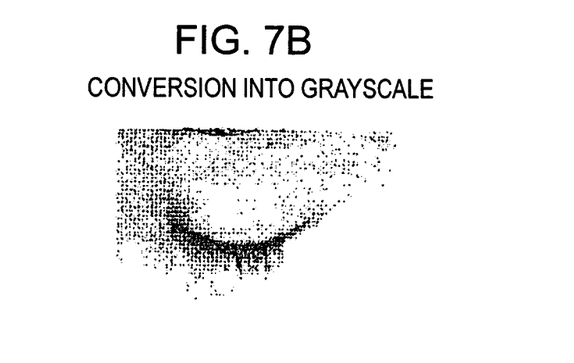
Figure 7C:
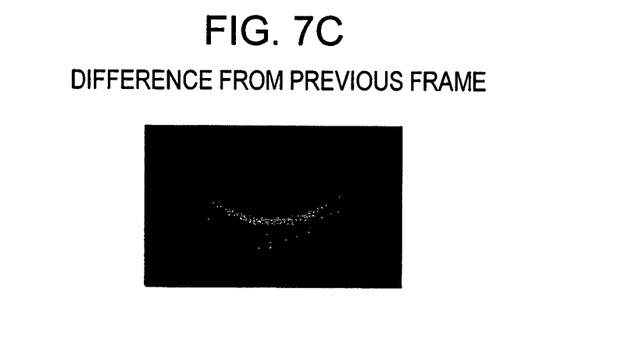

In this analysis circuit 13, for example, signal processing shown in FIGS. 7A, 7B, and 7C is performed (FIG. 7A shows only the area C containing the eye and the eyelid of the viewer). That is, the video signal (FIG. 7A) supplied from the video camera 12 is converted into grayscale (FIG. 7B), and the difference between the video signal that is converted into gray and the previous video signal (FIG. 7C) that is converted into gray is extracted. Therefore, the video signal of the difference indicates the portion where there is a movement within the image obtained by image-capturing the viewer. Then, the video signal of the difference is analyzed to output the bio-information, such as the body movement, the respiration, and the blinking, and this bio-information is supplied to the microcomputer 20.

Therefore, thereafter, as a result of performing processing described with reference to section (1), the arousal level and the concentration level of the viewer with respect to the object can be estimated and also, on the basis of the estimation results, the video and the sound can be reproduced in a state most appropriate for the psychological state of the viewer at that time.

Also, in this case, since the bio-information of the viewer can be obtained in a non-contact manner and in an unrestricted manner, the viewer is not made to have psychological and physical burdens, and no influence appears in the measurement results.

(3) Computation of Arousal Level and Concentration Level

At which position in FIG. 5 the arousal level and the concentration level of the viewer are currently positioned can be known by the processings of sections (3-1) and (3-2) described below. When the current arousal level and the current concentration level of the viewer are, for example, at the point P in FIG. 5, in which way of the curve D containing the point P the arousal level and the concentration level are directed can be determined on the basis of the history of the changes in the arousal level and the concentration level.

Therefore, it is possible to typically provide video and sound most appropriate for the current state of the viewer. Furthermore, when the state of the viewer is satisfactory, this can be maintained, and when the state of the viewer is unsatisfactory, this can be suppressed.

(3-1) Computation of Arousal Level

The arousal level can be determined from the variations with respect to the initial values or the standard values of the respiration rate and the pulse rate. That is, the arousal level can be computed from the following:

$$\text{the arousal level} = Rrm - Rrr \quad (1)$$

where Rrm is the measured value of the respiration rate per unit time, and Rrr is the initial value or the standard value of the respiration rate per unit time, or $$\text{the arousal level} = Prm - Prr \quad (2)$$

where Prm is the measured value of the pulse rate per unit time, and Rrr is the initial value or the standard value of the pulse rate per unit time.

(3-2) Computation of Concentration Level

The concentration level with respect to an object can be computed from the blinking of the eyelid on the basis of, for example, equation (3) or (4) below:

$$\text{the concentration level} = -(Nebm - Neb\_init) \quad (3)$$

where Nebm is the measured value of the blinking rate, and Neb_init is the initial value of the blinking rate, or $$\text{the concentration level} = -(Nebm - Neb\_ref) \quad (4)$$

where Neb_ref is the standard value of the blinking rate.

(4) Others

In the foregoing, when the video signal or the sound signal is modified on the basis of the estimation results of the psychological state of the viewer and the intensity thereof, the reproduction speed, the sound volume, the color, the content, etc., can be changed. Furthermore, the measured bio-information, and the video signal and/or the sound signal that are modified on the basis of the bio-information can also be recorded on a recording medium.

As a recording medium therefor, the hard disk device 24, an optical disc, a magneto-optical disc, a magnetic tape, a hard disk, a semiconductor memory, an IC card, etc., can be used. The recording optical disc can be a CD-R, a CD-RW, an MD, a DVD±R, a DVD±RW, a DVD-RAM, a Blue-ray disc, etc. Although the video signal and the sound signal are modified on the basis of the bio-information, the permission and the prohibition for changing the signals can be made selectable.

It should be understood by those skilled in the art that various modifications, combinations, sub-combinations and alterations may occur depending on design requirements and other factors insofar as they are within the scope of the appended claims or the equivalents thereof.

What is claimed is:

1. A bio-information processing apparatus comprising:
    a bio-information sensor that measures bio-information of a subject only in a non-contact manner and in an unrestricted manner, wherein the subject is a viewer of content comprising a video signal and a sound signal reproduced by a reproduction apparatus;
    a bio-information analysis circuit that estimates a psychological state of the subject and an intensity of the psychological state as a reaction of the subject to the video and sound signals based on at least one measured value of the bio-information measured using the bio-information sensor and based on an initial value or a standard value of the bio-information to generate an estimation result; and
    a control circuit that, in response to the estimation result, automatically modifies the video signal and/or the sound signal reproduced by the reproduction apparatus by:
        when the estimation result indicates that the subject is dissatisfied with the video signal and/or the sound signal, a luminance and a contrast of the video signal are decreased while the video signal continues to be reproduced by the reproduction apparatus, and a volume of the sound signal is decreased while the audio signal continues to be reproduced by the reproduction apparatus, and
        when the estimation result indicates that the subject is interested with the video signal and/or the sound signal, the luminance and the contrast of the video signal are increased and the volume of the sound signal is increased.

2. The bio-information processing apparatus according to claim 1, wherein the bio-information sensor is a video camera or an infrared video camera.

3. The bio-information processing apparatus according to claim 1, wherein the bio-information sensor is a sensor for measuring at least one of body movement, respiration, a heartbeat, a pulse, blinking, and a body surface temperature of the subject.

4. The bio-information processing apparatus according to claim 1, wherein the psychological state of the subject further comprises at least one of an interest, emotion, and feelings of the subject.

5. The bio-information processing apparatus according to claim 1, wherein the psychological state of the subject is determined from changes in at least one of a heartbeat rate, respiration rate, and blinking rate of the subject.

6. A reproduction apparatus comprising:
    reproduction device for reproducing a video signal and a sound signal;
    a bio-information sensor for measuring bio-information of a viewer of content comprising the video signal and the sound signal reproduced by the reproduction apparatus only in a non-contact manner and in an unrestricted manner;
    a bio-information analysis circuit for estimating a psychological state of the viewer and an intensity of the psychological state as a reaction of the subject to the video and sound signals based on at least one measured value of the bio-information measured using the bio-information sensor and based on an initial value or a standard value of the bio-information to generate an estimation result; and
    a control circuit that, in response to the estimation result, automatically modifies the video signal and/or the sound signal reproduced by the reproduction apparatus by:
        when the estimation result indicates that the subject is dissatisfied with the video signal and/or the sound signal, a luminance and a contrast of the video signal are decreased while the video signal continues to be reproduced by the reproduction apparatus and a volume of the sound signal is decreased while the audio signal continues to be reproduced by the reproduction apparatus, and
        when the estimation result indicates that the viewer is interested with the video signal and/or the sound signal, the luminance and the contrast of the video signal are increased and the volume of the sound signal is increased.

7. The reproduction apparatus according to claim 6, wherein the bio-information sensor is a video camera or an infrared video camera.

8. The reproduction apparatus according to claim 6, wherein the bio-information sensor is a sensor for measuring at least one of body movement, respiration, a heartbeat, a pulse, blinking, and a body surface temperature of the viewer.

9. The reproduction apparatus according to claim 6, wherein the psychological state of the viewer further comprises at least one of an interest, emotion, and feelings of the viewer.

10. The reproduction apparatus according to claim 6, wherein the psychological state of the viewer is determined from changes in at least one of a heartbeat rate, respiration rate, and blinking rate of the viewer.

11. The reproduction apparatus according to claim 6, wherein the a control circuit, in response to the estimation result, modifies at least one of a reproduction speed, color, and content of the signal.

12. The reproduction apparatus according to claim 6, further comprising recording means configured to record the bio-information and the sound signal and/or the video signal that are modified based on the estimation result.

13. The reproduction apparatus according to claim 12, wherein the recording means is one of an optical disc, a magneto-optical disc, a magnetic tape, a hard disk, a semiconductor memory, and an integrated circuit card.

14. The reproduction apparatus according to claim 12, wherein the optical disc is one of a compact disk-recordable, a compact disk-rewritable, a mini disc, a digital versatile disk±recordable, a digital versatile disk±rewritable, a digital versatile disk-random access memory, a multiple layer recordable disk, and a high definition recordable disc.

15. The reproduction apparatus according to claim 6, wherein prohibition and permission of a function for changing the video signal and/or the sound signal in accordance with the estimation result can be selected by a user.

16. A reproduction apparatus comprising:
a reproduction section that reproduces a video signal and a sound signal;
a bio-information sensor that measures bio-information of a viewer of content comprising the video signal and the sound signal reproduced by the reproduction section only in a non-contact manner and in an unrestricted manner;
a bio-information analysis circuit that estimates a psychological state of the viewer and an intensity of the psychological state based on at least one measured value of the bio-information measured using the bio-information sensor and based on an initial value or a standard value of the bio-information to generate an estimation result; and
a control device operable to:
cause the video signal and/or the sound signal reproduced by the reproduction section to be automatically modified in response to the estimation result of the bio-information analysis circuit;
when the estimation result indicates that the viewer is dissatisfied with the video signal and/or the sound signal, decrease a luminance and a contrast of the video signal while the video signal continues to be reproduced by the reproduction apparatus and decrease a volume of the sound signal while the audio signal continues to be reproduced by the reproduction apparatus; and
when the estimation result indicates that the viewer is interested with the video signal and/or the sound signal, increase the luminance and the contrast of the video signal and increase the volume of the sound signal.

17. The bio-information processing apparatus according to claim 1, wherein the reproduction apparatus comprises a DVD player.

18. The reproduction apparatus according to claim 6, wherein the reproduction device comprises a DVD player.

19. The reproduction apparatus according to claim 16, wherein the repro. duction section comprises a DVD player.

* * * * *